(12) United States Patent
Hackner

(10) Patent No.: US 9,138,552 B2
(45) Date of Patent: Sep. 22, 2015

(54) CLOSED SUCTIONING AND RINSING METHODS AND TRACHEAL DEVICES

(75) Inventor: Dani Hackner, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 354 days.

(21) Appl. No.: 12/602,992

(22) PCT Filed: Jun. 5, 2008

(86) PCT No.: PCT/US2008/065980
§ 371 (c)(1),
(2), (4) Date: Dec. 3, 2009

(87) PCT Pub. No.: WO2008/151298
PCT Pub. Date: Dec. 11, 2008

(65) Prior Publication Data
US 2010/0170517 A1    Jul. 8, 2010

Related U.S. Application Data

(60) Provisional application No. 60/942,180, filed on Jun. 5, 2007.

(51) Int. Cl.
*A61M 16/04*    (2006.01)
(52) U.S. Cl.
CPC ........... *A61M 16/04* (2013.01); *A61M 16/0479* (2014.02); *A61M 16/0434* (2013.01)
(58) Field of Classification Search
CPC ............ A61M 1/0023; A61M 1/0058; A61M 3/0262; A61M 16/04; A61M 16/0434; A61M 16/0463; A61M 16/0475; A61M 16/0477; A61M 16/04769; A61M 16/0486
USPC ........................ 128/200.26, 205.19, 205.25, 128/207.14–207.17; 604/23, 27, 28, 30, 32, 604/33, 35, 43, 45; 222/1, 71, 94, 129.4, 222/133; 417/470, 569, 570
See application file for complete search history.

(56) References Cited

U.S. PATENT DOCUMENTS

| | | | | |
|---|---|---|---|---|
| 4,240,417 A * | 12/1980 | Holever | ................... | 128/203.12 |
| 5,277,175 A * | 1/1994 | Riggs et al. | ............. | 128/200.21 |
| 5,449,348 A * | 9/1995 | Dryden | ........................ | 604/171 |
| 5,819,723 A * | 10/1998 | Joseph | ..................... | 128/207.14 |
| 5,899,877 A * | 5/1999 | Leibitzki et al. | ................ | 604/23 |
| 6,227,200 B1 * | 5/2001 | Crump et al. | ............ | 128/207.16 |

(Continued)

OTHER PUBLICATIONS

Paul-Allen et al., Survey of Nursing Practices With Closed-System Suctioning, American Journal of Critical Care, (Jan. 2000), 9(1):9-17.

(Continued)

*Primary Examiner* — Justine Yu
*Assistant Examiner* — Michael Tsai
(74) *Attorney, Agent, or Firm* — Seth D. Levy; Brian T. Duke; Nixon Peabody LLP

(57) ABSTRACT

Described herein is a method and apparatus that may be used in various applications, such as medical treatment of humans and animals. Among other things, the invention teaches a method for evacuating secretions in the trachea of a patient during endotracheal intubation by incorporating the use of a novel closed suctioning tracheal device containing a dedicated primary liquid reservoir, and a liquid chamber for supplying the liquid for lavage.

16 Claims, 2 Drawing Sheets

(56) References Cited

U.S. PATENT DOCUMENTS 6,907,879 B2 * 6/2005 Drinan et al. ............ 128/202.22
2005/0279359 A1 * 12/2005 LeBlanc et al. .......... 128/207.14

OTHER PUBLICATIONS

Blackwood et al., Closed Tracheal Suctioning Systems and Infection Control in the Intensive Care Unit, Journal of Hospital Infection, (Aug. 1998), 39(4):315-321.

Klockare et al., Comparison Between Direct Humidification and Nebulization of the Respiratory Tract at Mechanical Ventilation: Distribution of Saline Solution Studied by Gamma Camera, Journal of Clinical Nursing, (Mar. 2006), 15(3):301-307.

Puchalski et al., Should Normal Saline be Used When Suctioning the Endotracheal Tube of the Neonate?, Medscape, Internet Response posted Mar. 14, 2007, (www.medscape.com/viewarticle/552862).

Kollef, M., Respiratory Failure: Complications of Mechanical Ventilation, ACP Medicine Online, (posted Sep. 1, 2002).

* cited by examiner

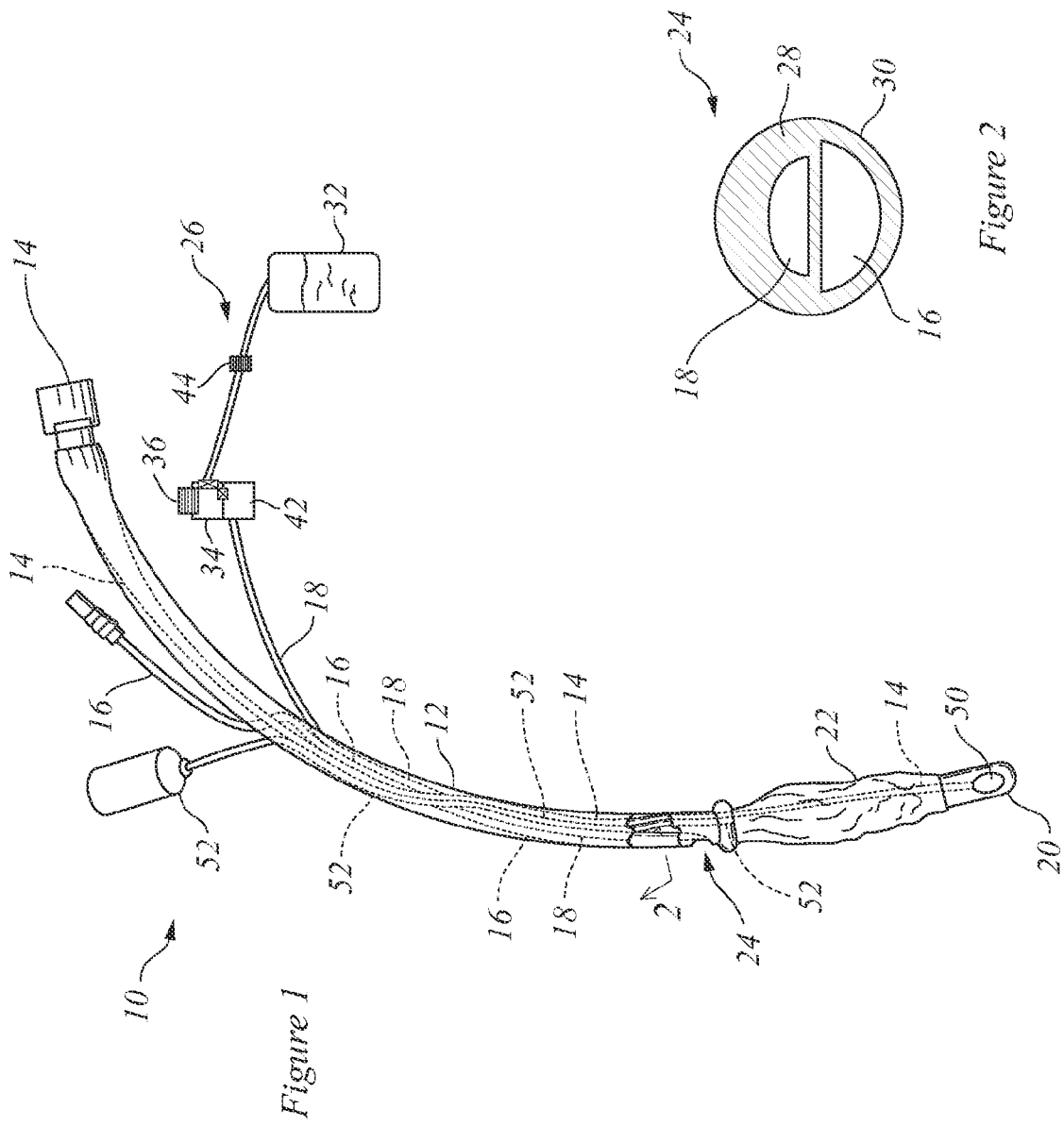

CLOSED SUCTIONING AND RINSING METHODS AND TRACHEAL DEVICES

This application is the National Phase of International Application PCT/US08/65980, filed Jun. 5, 2008, which designated the U.S. and that International Application was published under PCT Article 21(2) in English. This application also includes a claim of priority under 35 U.S.C. §119(e) to U.S. provisional patent application No. 60/942,180, filed Jun. 5, 2007.

FIELD OF THE SUBJECT MATTER

The present subject matter relates to devices and methods used for rinsing and evacuation of secretions in the tracheal tube of an intubated patient. In particular, the present subject matter relates to closed suction tracheal devices containing a dedicated primary liquid reservoir connected to the device, and a volume measuring liquid chamber, for supplying liquid for rinsing.

BACKGROUND OF THE SUBJECT MATTER

All publications herein are incorporated by reference to the same extent as if each individual publication or patent application was specifically and individually indicated to be incorporated by reference. The following description includes information that may be useful in understanding the present subject matter. It is not an admission that any of the information provided herein is prior art or relevant to the presently claimed subject matter, or that any publication specifically or implicitly referenced is prior art.

Endotracheal intubation involves the insertion of a flexible plastic tubular device, known as an endotracheal tube, into the trachea of a patient to protect the patient's airway and provide a means of mechanical ventilation. The most common method teaches the passing of an endotracheal tube, with the assistance of a laryngoscope, through the mouth, larynx, and vocal cords into the trachea, terminating at a position above the carina.

The primary purposes of endotracheal intubation, are to mechanically ventilate the patient's lungs, when a disease prevents the patient from normal, breathing induced ventilation, or to apply anesthetic gases during surgical intervention. In order to create enough air pressure to accomplish such mechanical ventilation and to prevent the escape of gases past the tube, it is necessary to seal the passageway around the endotracheal tube. A seal may be produced by the use of an inflatable cuff formed integrally with and surrounding the endotracheal tube. When the endotracheal tube has been introduced into the patient's trachea, the inflatable cuff will normally be located a few centimeters above the carina and within the tube-like trachea. The inflatable cuff is then inflated so as to engage the wall of the trachea and to help secure it in place and protect the airway from blood, vomit, and secretions. Gases may then be introduced through the endotracheal tube and into the lungs of the patient.

Although tracheal tubes have been effectively used in treating patients requiring respiratory ventilation, there exist several complications which may cause pneumonia, infections and other ailments when employing tracheal tubes.

In particular, many patients receiving endotracheal intubation develop complications, resulting from an infection of the lungs, possibly induced by contaminated, pooled secretions entering the trachea and the lungs. Infectious secretions may also reach the lungs upon cessation of mechanical ventilation, particularly when the need for endotracheal intubation ends and the inflatable cuff of the endotracheal tube is deflated allowing the infectious secretions, which have pooled above the inflatable cuff, to flow into the lungs. In certain instances, infectious secretions may reach the lungs during intubation, generally by aspiration of the secretions past the tracheal tube cuff.

Endotracheal suctioning is a common and effective procedure performed in patients receiving endotracheal intubation. In performing endotracheal suctioning, secretions accumulated in the tracheobronchital tree of the patient are cleared, leading to reduced incident and frequency of infection and other complications due to accumulation of secretions. In addition, endotracheal suctioning promotes optimal oxygenation of the lungs. However, endotracheal suctioning has been known to have adverse effects; primarily, the microbial contamination of the airway and lungs, and development of ventilator-associated pneumonia.

Two methods of endotracheal suctioning are currently available in the art, the open suction system and closed suction system. The open suction system ("OSS") has been in use since the late 1970's, and is a single-use device intended to be disposed of after use. The open suction system requires the sealed ventilator circuit to be broken for enactment of endotracheal suctioning, allowing for possible contamination and infection of both the caregiver and the patient. The closed suction system ("CSS") was introduced to limit the problems of contamination and infection associated with OSS and allow for the ventilator circuit to stay intact while performing endotracheal suctioning. In addition, CSS may be complemented with the integration of a suction tube within the tracheal tube to allow for the suction tube to remove pooled secretions from the pulmonary area via endotracheal suctioning, without disconnecting the patient from the ventilation system, thus reducing the incidence of infection.

Based on advantages such as lower incidence of ventilator associated pneumonia, fewer physiological disturbances, decreased microbiological contamination, and lower cost, CSS has become increasingly popular in the past decade, and accounts for the vast majority endotracheal suctioning used in the United States. (Paul-Allen et al., Survey of Nursing Practices With Closed-System Suctioning, American Journal of Critical Care, (January 2000), 9(1):9-17)

However, the progression of endotracheal suctioning methods from OSS to CSS, and further safe-guards produced in an attempt to reduce the rate of infection, have not entirely eliminated incidents of infection and contamination, and numerous patients continue to suffer from shortcomings employed in the current technology.

For example, CSS commonly employs a cavity found within the CSS system that allows a caregiver to inject liquid (such as saline) into the circuit or airway before, during or after the suction procedure. As the injection requires a break in the system, the CSS is compromised allowing for contamination. As a contaminated syringe, a contaminated liquid, or contaminated equipment associated with either the syringe or liquid, may be the culprit for infection, the incidence and possibility of disseminating a pathogen remains a primary health concern.

Furthermore, in the current CSS method, sterility may be compromised due to contact between a caretakers contaminated glove and the CSS cavity or syringe, when adding liquid or handling the CSS cavity (Blackwood et al., Closed Tracheal Suctioning Systems And Infection Control In The Intensive Care Unit, Journal Of Hospital Infection, (August 1998), 39(4):315-321). Accidental contamination as a result of improper cleaning procedures of the suction system is yet another cause of infection and contamination.

In both OSS and CSS, there exists the necessity to soften up the pooled secretions to ensure optimal removal via suction. In order to facilitate the removal of pooled secretions from the pulmonary area, a liquid solution, such as saline, is commonly administered to the pulmonary area to increase the efficacy of endotracheal suctioning. Saline solution has been shown to effectively "thin out" the secretions and to assist in their removal (Klockare et al., Comparison Between Direct Humidification And Nebulization Of The Respiratory Tract At Mechanical Ventilation: Distribution Of Saline Solution Studied By Gamma Camera, Journal of Clinical Nursing, (March 2006), 15(3):301-307). Once the secretions are thinned out, both the liquid and secretions are aspired from the trachea and surrounding areas by the chosen endotracheal suctioning means.

However, complications have arisen in connection with the administration and application of liquid solution to patients. Patients who have experienced endotracheal suctioning describe it as profoundly unpleasant and even a painful experience. The experience of saline instillation has been described as feeling "like I was drowning." (Puchalski et al., Should Normal Saline be Used When Suctioning the Endotracheal Tube of the Neonate?, Medscape, Internet response posted Mar. 14, 2007. Unfortunately, this all too common experience is often caused by the over-administration of liquid to the patient by a caretaker.

As a result of the deficiencies prevalent in the current CSS and OSS methods, patients mechanically ventilated by tracheal devices remain at considerable risk for infection and contamination, diminishing the quality of care afforded to patients and causing unnecessary discomfort and pain (Kollef, M., Respiratory Failure: Complications of Mechanical Ventilation, ACP Medicine Online, (posted Sep. 1, 2002)). The incidence of infection and complications associated with infections are further exacerbated by the inaccurate administration of liquid solution, a common practice performed prior to endotracheal suctioning.

Accordingly, there exists a need in the art for devices and methods capable of substantially reducing the incidence of infection and spread of infectious agents during endotracheal intubation, as well as administering the precise quantity of liquid solution for secretion softening for improved suctioning.

The present subject matter addresses the inadequacies of current intubation methods by introducing a dedicated primary liquid reservoir attached to an endotracheal suctioning system by means of appropriate valves, and a volume measuring liquid chamber device, thus providing a composite closed suctioning and rinsing method that prevent uncontrolled flow of liquid. Because the design is truly closed, sterility is never compromised by exposing the system or introducing outside elements, such as liquid for rinsing, into the system. Furthermore, because the volume of liquid delivered for rinsing is controlled, the patient never receives an excess quantity of liquid.

BRIEF DESCRIPTION OF THE FIGURES

Exemplary embodiments are illustrated in the referenced figures. It is intended that the embodiments and figures disclosed herein are to be considered illustrative rather than restrictive.

FIG. 1 depicts a front perspective view of the tracheal tube in accordance with an embodiment of the subject matter.

FIG. 2 depicts a front perspective view of the tracheal tube cavity in accordance with an embodiment of the subject matter.

DETAILED DESCRIPTION OF THE SUBJECT MATTER

Figure 3:
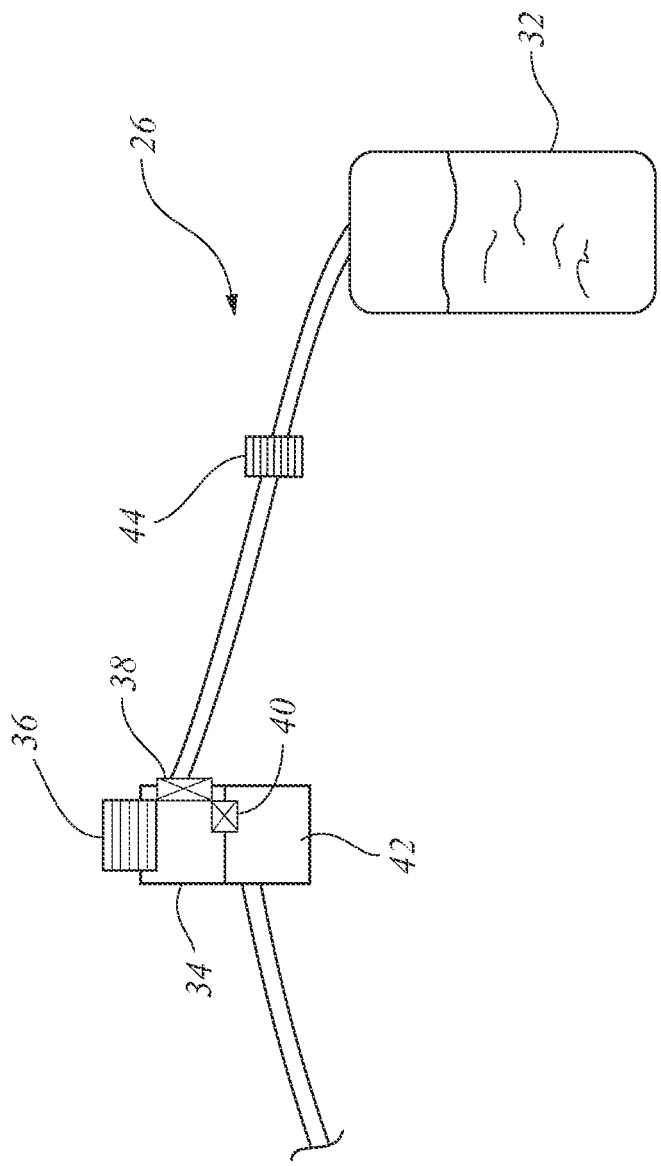
FIG. 3 depicts an expanded view of the metered liquid mechanism in accordance with an embodiment of the subject matter.

All references cited herein are incorporated by reference in their entirety as though fully set forth. Unless defined otherwise, technical and scientific terms used herein have the same meaning as commonly understood by one of ordinary skill in the art to which this subject matter belongs.

One skilled in the art will recognize many methods, devices or materials similar or equivalent to those described herein, which could be used in the practice of the present subject matter. Indeed, the present subject matter is in no way limited to the methods, devices or materials described.

The present subject matter addresses the shortcomings of current endotracheal suctioning systems by providing a dedicated primary liquid reservoir connected to a closed suction system by means of appropriate valves and a volume measuring liquid chamber. Furthermore, the subject matter discloses a composite design of a totally inline suctioning and rinsing method that does not allow the free flow of liquid. The end result of the subject matter is a truly closed suction system that does not require the breaking of seals to suction or rinse the tracheal region with liquid. Consequently, caregiver handling and application of liquid solution is abolished, eliminating the risk of infection through a liquid cavity or bulb, and over-administration of liquid to the patient.

Referring to FIG. 1, a tracheal tube 10 in accordance with one embodiment of the present subject matter is depicted. The tracheal tube 10 is adapted to fit a patient's airway and consists of a multi-tube cannula 12 containing at least one respiratory tube 14, at least one suction tube 16, and at least one rinse tube 18 attached to a metered liquid mechanism 26. In the embodiment, each of these tubes is at least partially internal to the multi-tube cannula 12. The respiratory tube 14 extends through the entire multi-tube cannula 12 and is adapted to mechanically ventilate a patient (not shown). Accordingly, a respiratory end 20 of the multi-tube cannula 12 is configured to rest in the upper respiratory system of the patient, and contains an aperture 50 for mechanical ventilation of the patient's lungs. An inflatable cuff 22 encapsulates the multi-tube cannula 12 near the respiratory end 20 and is designed to obstruct the patient's airway at the trachea, once inflated. An inflation device 52, which is partially internal to the multi-tube cannula 12, is coupled to the inflatable cuff 22 for inflation and deflation of the inflatable cuff 22. The function of the inflatable cuff 22 is to eliminate or at least to minimize the undesirable flow of fluids from above the tracheal region of the patient into the bronchi and lungs of the patient.

The tracheal tube 10 contains a cavity 24 found on the respiratory end 20 of the tracheal tube 10, just above the inflatable cuff 22. The cavity 24 traverses the suction tube 16 through a wall 28 of the multi-tube cannula 12 to an exterior surface 30 of the multi-tube cannula 12. Accordingly, the suction tube 16 is adapted to suction fluids that collect above the inflatable cuff 22 in the patient. The rinse tube 18 also traverses the multi-tube cannula 12 and terminates at the cavity 24 for introduction of rinse liquid in the area above the inflatable cuff 22. Moreover, the rinse tube 18 may terminate proximate to the cavity 24, for introduction of a rinse liquid. The rinse liquid introduced by the rinse tube 18 is collected by the suction tube 16 while the suction tube 16 is suctioning or otherwise evacuating the area above the inflatable cuff 22.

The rinse tube 18 and suction tube 16 are situated so as to introduce the rinse liquid to the area containing secretions and suction away the combined pooled liquids and other potentially clogging secretions contained in the area above and around the inflatable cuff 22.

The rinse liquid, introduced to secretions through the rinse tube 18, is supplied by the metered liquid mechanism 26. As shown in the expanded view of the metered liquid mechanism 26 in FIG. 3, the metered liquid mechanism 26 comprises a primary liquid reservoir 32 which supplies the liquid to a liquid chamber 34. A spring loaded button operated valve 36 controls a first one-way valve 38 between the liquid reservoir 32 and the liquid chamber 34, and also controls a second one way valve 40 between the liquid chamber 34 and a rinse chamber 42. The rinse chamber 42 is operationally connected to the rinse tube 18 and introduces the rinse liquid to the rinse tube 18. When the button operated valve 36 is in an unpressed configuration, the first one-way valve 38 is open and serves to allow filling of the liquid chamber 34 with liquid. When the button operated valve 36 is then depressed, the first one way valve 38 closes and the second one way valve 40 opens allowing the measured volume of liquid in the liquid chamber 34 to flow through the rinse chamber 42 and ultimately to the rinse tube 18. Once in the rinse tube 18, the rinse liquid is introduced through the cavity 24 for dilution of secretions, and is ultimately vacuumed up with the secretions by the suction tube 16.

The dedicated sterile liquid reservoir 32 is controlled by a separate stopvalve 44 as it fills the liquid chamber 34. The stopvalve 44 prevents liquid flow into the liquid chamber 34 between rinse procedures, thereby allowing the liquid chamber 34 to be left empty and dry between suction-rinse procedures. This further reduces the possibility of cross contamination since it is much more difficult to contaminate a dry chamber. When the stopvalve 44 is closed and the button operated valve 36 is activated, the liquid chamber 34 is emptied into the rinse chamber 42. However, as no liquid enters the liquid chamber 34 when the button operated valve 36 is released, the liquid chamber 34 is evacuated of fluid reducing the risk of contamination. As a result, a truly closed-suction system that does not require the breaking of seals to suction or rinse is achieved. The closed-suction system of the present device receives its fluid from the liquid chamber 34 filled with liquid from the dedicated reservoir 32. Consequently, no caregiver handling of a cavity is necessary and because each press of the button operated valve 36 releases only a pre-measured volume of liquid, there is no danger of administering excess liquid to the patient. When the dedicated sterile liquid reservoir 32 becomes emptied, it is easily replaced without compromising sterility or opening the system.

In alternative embodiments, the rinse liquid may comprise water, saline, as well as some other biocompatible liquids. A medicament, for example, an antiseptic or an antibiotic, or a treatment such as a surfactant may be added to the rinse liquid to obtain a desired effect on the patient, or to ease suctioning and/or cleaning of the suction tube 16.

In operational use of the device, the clinician would insert the tracheal tube 10 into the patient's trachea 46 in a manner known and understood by those of skill in the art. The cuff 22 would be inflated by the inflation device 52, sealing the tracheal tube 10 within the walls 48 of the patient's trachea 46. Ventilation of the patient through the respiratory tube 14 would likely commence at this time. At the discretion of the clinician, the metered liquid mechanism 26 would be prepared for operation by opening the stopvalve 44. At this time, a first one way valve 38 between the liquid reservoir 32 and the liquid chamber 34 is open; however, because the liquid chamber 34 is otherwise closed, air in the liquid chamber 34 generally prevents liquid from flowing in. To activate the system, the clinician would depress the button operated valve 36 which closes the first one way valve 38 and opens a second one way valve 40 between the liquid chamber 34 and the rinse chamber 42. This results in a partial vacuum in the liquid chamber 34. When the button operated valve 36 is released (closing the second one way valve 40 and opening the first one way valve 38), liquid is drawn into and fills the liquid chamber 34 (with the total volume of liquid being limited to the volume of the liquid chamber 34). Upon each subsequent depression of the button operated valve 36, a measured volume of liquid is released into the rinse chamber 42 for lavage and rinse procedures. With each release of the button operated valve 36, the liquid chamber 34 refills. This permits simple one handed control of liquid release. When the washing procedure is complete, the stopvalve 44 is closed and the button operated valve 36 is operated one more time to drain the liquid chamber 34 and rinse chamber 42 and leave both chambers empty so that there is no fluid volume left to contact the tracheal tube.

In another embodiment, the rinse liquid may incorporate other solutions such as a medicament, for example, an antiseptic or an antibiotic. In such cases, it may be desirable to allow the rinse liquid to remain amongst the secretions for an extended period of time so as to gain the desired therapeutic effect prior to suctioning.

In yet another embodiment, the present subject matter may be advantageous in cohorted and non-cohorted areas. In cohorted areas there is a higher risk of exposure to staff and caretakers, who are not infected but surrounded by infected patients. The true closed suction system disclosed in the present subject matter substantially reduces the incidence of infection by reducing the need for staff and caretakers to contact the infected patients, and the intubation devices affixed to the infected patients. In non-cohorted areas infection is spread primarily due to procedural laxity and lack of awareness by staff and caretakers. Chance, sporadic spread in non-cohorted areas is prevented by reducing the need for physical contact between patients and staff when tending to tracheal devices affixed to the infected patients. By eliminating the transfer points of infection, rather than relying upon staff and caretaker training and procedural diligence, which may not be as strong without frequent reinforcement from daily work within cohorted areas, the present subject matter reduces the incidents of infection. Thus, the present subject matter significantly reduce the spread of infection in cohorted and non-cohorted areas caused by the handling of intubation devices by staff and caretakers.

The present subject matter is also directed to a kit for endotracheal intubation, intended for, but in no way limited to, (1) mechanical ventilation of a patient's lungs, and/or (2) introduction of anesthetic gases to a patient's lungs. The kit is useful for practicing the inventive methods of treating such conditions. The kit is an assemblage of materials or components, including at least one of the inventive compositions. Thus, in some embodiments the kit contains a component including a closed suction tracheal device containing a dedicated primary liquid reservoir connected to the device, or a volume measuring liquid chamber for supplying liquid for rinsing, as described above.

The exact nature of the components configured in the inventive kit depends on its intended purpose. For example, some embodiments are configured for the purpose of furnishing a dedicated primary liquid reservoir to an endotracheal intubation device. The kit may be configured particularly for the purpose of furnishing a volume measuring liquid chamber for supplying liquid for rinsing. In further embodiments, the kit may be configured for veterinary applications, for use in treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to enact endotracheal intubation. Optionally, the kit also contains other useful components such as saline solution, a catheter, a laryngoscope, an applicator, bandaging material or other useful paraphernalia as will be readily recognized by those of skill in the art.

The materials or components assembled in the kit can be provided to the practitioner stored in any convenient and suitable ways that preserve their operability, sterility and/or utility. The components are typically contained in suitable packaging material(s). As employed herein, the phrase "packaging material" refers to one or more physical structures used to house the contents of the kit, such as inventive components and the like. The packaging material is constructed by well known methods, preferably to provide a sterile, contaminant-free environment. The packaging materials employed in the kit are those customarily utilized for medical instruments. As used herein, the term "package" refers to a suitable solid matrix or material such as glass, plastic, paper, foil, and the like, capable of holding the individual kit components. Thus, for example, a package can be a plastic wrap used to contain components of the inventive subject matter. The packaging material generally has an external label which indicates the contents and/or purpose of the kit and/or its components.

The foregoing description of various embodiments of the subject matter known to the applicant at the time of filing this application has been presented and is intended for the purposes of illustration and description. The present description is not intended to be exhaustive nor limit the subject matter to the precise form disclosed and many modifications and variations are possible in light of the above teachings. The embodiments described serve to explain the principles of the subject matter and its practical application and to enable others skilled in the art to utilize the subject matter in various embodiments and with various modifications as are suited to the particular use contemplated. Therefore, it is intended that the subject matter disclosed herein not be limited to the particular embodiments disclosed.

While particular embodiments of the present subject matter have been shown and described, it will be obvious to those skilled in the art that, based upon the teachings herein, changes and modifications may be made without departing from this subject matter and its broader aspects and, therefore, the appended claims are to encompass within their scope all such changes and modifications as are within the true spirit and scope of this subject matter. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. An airway lavage device comprising:
   a tracheal tube adapted for placement in a patient's airway;
   a liquid chamber for delivery of liquid for lavage;
   a liquid reservoir connected to the liquid chamber for supplying liquid;
   a rinse chamber connected to the liquid chamber;
   a rinse tube found within the tracheal tube and adapted for deliverance of liquid for lavage of the patient's airway, the rinse tube connected to the rinse chamber;
   a first one way valve disposed between the liquid reservoir and the liquid chamber;
   a stopvalve located between the liquid reservoir and the first one way valve;
   a second one way valve disposed between the liquid chamber and the rinse chamber; and
   a spring loaded button connected to both the first one way valve and the second one way valve, whereby when the button is not pressed, the first one way valve is open and the second one way valve is closed and when the button is pressed, the first one way valve is closed and the second one way valve is open.

2. The device according to claim 1, further comprising a respiratory tube found within the tracheal tube adapted to the patient's airway.

3. The device according to claim 1, further comprising a suction tube found within the tracheal tube for suctioning of the patient's airway.

4. The device according to claim 3, further comprising a liquid adapted to be flushed through the rinse tube and extracted by the suction tube.

5. An airway lavage device comprising:
   a tracheal tube for placement in a patient's airway;
   a respiratory tube found within the tracheal tube for mechanical ventilation of the patient's airway;
   a suction tube found within the tracheal tube for suctioning of the patient's airway;
   a liquid chamber for delivery of liquid for lavage;
   a liquid reservoir connected to the liquid measuring chamber for supplying liquid;
   a rinse chamber connected to the liquid chamber;
   a rinse tube found within the tracheal tube and adapted for deliverance of liquid for lavage of the patient's airway, the rinse tube connected to the rinse chamber;
   a first one way valve disposed between the liquid reservoir and the liquid chamber;
   a stopvalve located between the liquid reservoir and the first one way valve;
   a second one way valve disposed between the liquid chamber and the rinse chamber; and
   a spring loaded button connected to both the first one way valve and the second one way valve, whereby when the button is not pressed, the first one way valve is open and the second one way valve is closed and when the button is pressed, the first one way valve is closed and the second one way valve is open.

6. The device according to claim 5, further comprising a liquid adapted to be flushed through the rinse tube and extracted by the suction tube.

7. An airway lavage device comprising:
   a liquid chamber for delivery of liquid fbr lavage;
   a liquid reservoir connected to the liquid chamber for supplying liquid;
   a rinse chamber connected to the liquid chamber;
   a rinse tube connected to the rinse chamber and adapted for the deliverance of liquid for lavage of the patient's airway;
   a first one way valve disposed between the liquid reservoir and the liquid chamber;
   stopvalve between the liquid reservoir and the first one way valve;
   a second one way valve disposed between the liquid chamber and the rinse chamber; and a spring loaded button connected to both the first one way valve and the second one way valve, whereby when the button is not pressed, the first one way valve is open and the second one way valve is closed and when the button is pressed, the first one way valve is closed and the second one way valve is open.

8. The device according to claim 7, further comprising a liquid adapted to be flushed through the rinse tube.

9. A method of evacuation of secretions in the tracheal pathway of a patient during endotracheal intubation comprising:

providing a device comprising:

a tracheal tube adapted for placement in a patient's airway;

a respiratory tube found within the tracheal tube for mechanical ventilation of the patient's airway a suction tube found within the tracheal tube for suctioning of the patient's airway;

a liquid chamber for delivery of liquid for lavage;

a liquid source connected to the liquid chamber supplying liquid;

a rinse chamber connected to the liquid chamber;

a rinse tube found within the tracheal tube and adapted for deliverance of liquid for lavage of the patient's airway, the rinse tube connected to the rinse chamber a first one way valve disposed between the liquid reservoir and the liquid chamber;

a stopvalve between the liquid reservoir and the first one way valve;

a second one way valve disposed between the liquid chamber and the rinse chamber; and a spring loaded button connected to both the first one way valve and the second one way valve, whereby when the button is not pressed, the first one way valve is open and the second one way valve is closed and when the button is pressed, the first one way valve is closed and the second one way valve is open, inserting the tracheal tube into a patient's airway for intubation;

sealing the tracheal tube within the trachea of the patient;

ventilating the patient through the respiratory tube for mechanical ventilation of the patient;

pressing the spring loaded button, thereby emptying any contents of the liquid chamber, previously supplied to the liquid chamber by the liquid reservoir, into the rinse chamber;

dousing the tracheal pathway of a patient with the liquid, through the rinse tube for loosening secretions from the tracheal pathway; and suctioning secretions from the tracheal pathway of a patient through the suction tube.

10. The method of claim 9, wherein the liquid used for lavage is adapted to be flushed through the rinse tube and extracted by the suction tube.

11. The method of claim 9, wherein the liquid used for lavage comprises a biocompatible liquid such as water or saline.

12. The method of claim 9 wherein the liquid used for lavage comprises an antiseptic.

13. A method of evacuation of secretions in the tracheal pathway of a patient during endotracheal intubation comprising:

providing a device comprising:

a liquid chamber for delivery of liquid for lavage;

a liquid reservoir connected to the liquid chamber supplying liquid;

a rinse chamber connected to the liquid chamber;

a rinse tube connected to the rinse chamber and adapted for deliverance of liquid for lavage of the patient's airway;

a first one way valve disposed between the liquid reservoir and the liquid chamber;

a stopvalve between the liquid reservoir and the first one way valve;

a second one way valve disposed between the liquid chamber and the rinse chamber; and a spring loaded button connected to both the first one way valve and the second one way valve, whereby when the button is not pressed, the first one way valve is open and the second one way valve is closed and when the button is pressed, the first one way valve is closed and the second one way valve is open, inserting the rinse tube into a patient's airway for delivery of liquid for lavage;

pressing the spring loaded button for activation of the liquid, thereby emptying any contents of the liquid chamber, previously supplied to the liquid chamber by the liquid reservoir, into the rinse chamber; and dousing the tracheal pathway of a patient with the liquid, through the rinse tube for loosening secretions from the tracheal pathway.

14. The method of claim 13, wherein the liquid used for lavage is adapted to be flushed through the rinse tube.

15. The method of claim 13, wherein the liquid used for lavage comprises a biocompatible liquid such as water or saline.

16. The method of claim 13 wherein the liquid used for lavage comprises an antiseptic.

* * * * *